United States Patent [19]

Williams

[11] Patent Number: 4,636,073

[45] Date of Patent: Jan. 13, 1987

[54] UNIVERSAL CALIBRATION STANDARD FOR SURFACE INSPECTION SYSTEMS

[75] Inventor: Randal R. Williams, Woodbridge, Va.

[73] Assignee: International Business Machines Corporation, Armonk, N.Y.

[21] Appl. No.: 666,588

[22] Filed: Oct. 31, 1984

[51] Int. Cl.[4] .............................................. G01N 21/88
[52] U.S. Cl. ..................................... 356/243; 356/237
[58] Field of Search ................ 356/237, 243, 38, 371; 250/252.1

[56] References Cited

U.S. PATENT DOCUMENTS

| | | | |
|---|---|---|---|
| 3,767,306 | 10/1973 | Mast et al. | 356/38 |
| 4,135,821 | 1/1979 | Pechin et al. | 356/335 |
| 4,215,939 | 8/1980 | Miller et al. | 356/371 |
| 4,386,850 | 6/1983 | Leahy | 356/237 X |
| 4,512,659 | 4/1985 | Galbraith et al. | 356/237 X |

OTHER PUBLICATIONS

C. A. Gaston, "Standard Wafer for Intensity and Focus Testing," *IBM Tehnical Disclosure Bulletin*, vol. 24, No. 11A, pp. 5587–5589, Apr. 1982.

C. S. Gati, "Calibration Standard for Oblique Light-Type Particle Detection/Measurement Instruments," *IBM Technical Disclosure Bulletin*, vol. 24A, No. 11B, pp. 6064–6067, Apr. 1982.

Technical Bulletin, No. 4, Tencor Instruments, Mar. 15, 1984.

R. Iscoff, "Wafer Defect Detection System," *Semiconductor International*, Nov. 1982, pp. 39–52.

Primary Examiner—Vincent P. McGraw
Assistant Examiner—S. A. Turner
Attorney, Agent, or Firm—Jesse L. Abzug; John E. Hoel

[57] ABSTRACT

A universal calibration standard for surface inspection systems has a plurality of hemispherical pads which simulate the liquid scattering due to particulate contamination. The hemispherical pads scatter light irrespective of angles of illumination and detection and of rotational orientation, and are fabricated using ball-limiting metallurgical techniques. Any number and sizes of pads can be arranged on a substrate and the standard can be repeatedly cleaned, thereby having a long useful life.

8 Claims, 5 Drawing Figures

UNIVERSAL CALIBRATION STANDARD FOR SURFACE INSPECTION SYSTEMS

BACKGROUND OF THE INVENTION

1. Technical Field

This invention relates to calibration standards for surface inspection systems.

2. Background Art

The need for the calibration of wafer surface inspection systems has been widely recognized by the semiconductor manufacturing industry. These systems are used for the detection, identification, and measurement of the number and sizes of particles on, or in, the surface of semiconductor wafers. The prior absence of a suitable calibration standard has resulted in skepticism regarding the daily performance and reliability of these instruments. In the prior art, there have been several attempts to fabricate a standard using a variety of known features to provide a light-scattering response that is comparable to the levels observed with particulate contamination. These features include the use of polystyrene (latex) spheres, etched pits/holes, raised frustums, and thin wires or fibers.

One of the most prevalent methods of establishing the sensitivity of these systems has been the atomization and deposition of a dilute suspension of monodisperse, polystyrene spheres in a random pattern upon the surface of a semiconductor wafer. Despite the availability, uniformity, and repeatability of these spheres, there are a number of problems associated with this method of calibration. The major limitation is that each sphere must be characterized as to its size and its location on the wafer using optical and/or electron microscopy. This long and tedious procedure is required to distinguish each sphere from either surface contamination, or from clusters of spheres that have agglomerated. The spacing between each sphere must also be considered, because if the spacing between two or more spheres is less than the resolution capabilities of the detector, then the spheres will not be resolved from one another and will be detected as a single, larger sphere. A further limitation is that when the wafer becomes heavily contaminated, it must be discarded because of the difficulty in distinguishing the spheres from the surface contamination.

Due to the numerous problems with using latex spheres, there have been several attempts to fabricate a substrate with an easily recognizable pattern of either etched pits (or holes) or raised frustums to simulate particulate contamination. Although these standards are permanent and capable of being cleaned of any surface contamination, there are some inherent disadvantage associated with there use. First, unless these features are circular in shape, their scattering responses will change with the orientation of the substrate within the system. Even if the features are circular, the response is still dependent upon the illumination and detection geometries of the instrument, since these features scatter light in an anisotropic manner. Therefore, these prior calibration standards have failed to have universal application, and can only serve as references for maintaining the repeatability of a specific type of wafer surface inspection system.

It is highly desirable to have a universal calibration standard which can be used not only as a reference for maintaining the repeatability of a specific type of wafer surface inspection system, but also to have universal application such that different types of wafer surface inspection systems can be readily compared and/or set at a common sensitivity.

DISCLOSURE OF THE INVENTION

Therefore, it is the object of this invention to provide an improved optical calibration standard which can be used on all types of optical inspection equipment.

It is a further object to provide an improved calibration standard that is independent of angles of illumination and detection and of rotational orientation.

It is an additional object to provide an optical calibration standard that can be regularly cleaned and reused.

It is a related object of this invention to provide an improved method for making an optical calibration standard.

In accordance with these objects, an improved universal calibration standard includes a patterned array of hemispherical solder dots, which are first evaporated onto the surface of a semiconductor wafer in the form of circular frustums, and then melted and cooled so that they form into uniform hemispheres. The reflectivity of such an array of hemispherical dots is uniform with respect to the angle of illumination and detection of the measuring instrument and also independent of the rotational orientation of the calibration standard.

BRIEF DESCRIPTION OF THE DRAWINGS

The foregoing and other advantages of the invention will be more fully understood with reference to the description of the best mode and the drawing wherein.

DESCRIPTION OF THE BEST MODE FOR CARRYING OUT THE INVENTION

Figure 1:
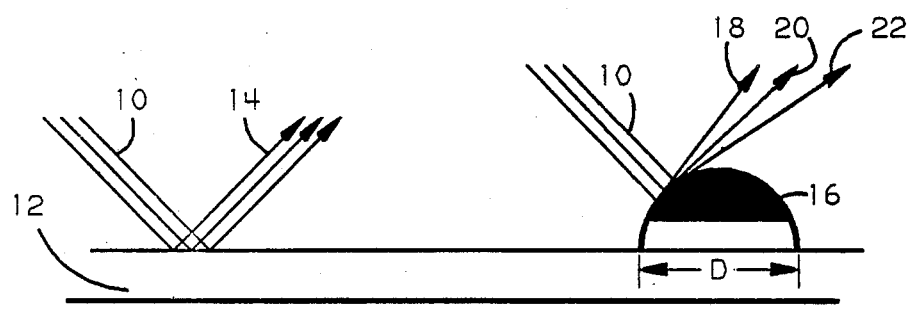
FIG. 1 shows diagrammatically a hemispherical pad on a substrate.

Referring to FIG. 1, conventional surface inspection systems use either bright-field and/or dark-field inspection techniques. In both cases light 10 striking the surface of a substrate 12 is reflected in a specular manner as shown by light beam 14. With the placement of a hemispherical pad 16 to simulate particulate contamination in the path of light 10, scattering in diffuse directions 18, 20 and 22 occurs.

The substrate 12 for the calibration standard ideally should have a highly reflective and exceptionally clean surface such that light will easily be reflected with a minimum of stray light scattering. A semiconductor wafer is chosen as the substrate in the preferred embodiment. The hemispherical pad 16 results from reflowing a circular metal frustum 24 (FIGS. 2a–c) at an elevated temperature. The hemispherical shape results from the interaction between the surface tension of a solder layer 26 and the adhesion forces between the solder 26 and underlying metallic layers 28. A primary consideration in producing hemispherical pads is the melting point and bonding properties of the solder layer 26. The solder should be relatively low melting, be capable of undergoing reflow, and be non-bonding to the selected substrate 12. Typical metals that have been used in other reflow applications include solder alloys of lead, tin, gold, indium, and/or bismuth. Pure tin is the primary choice for solder layer 26 since it is slightly harder and more durable than most lead alloys, and forms a thin, protective, surface layer of metal oxide when in contact with the atmosphere. An even better choice would be the use of pure gold, or a lower melting eutectic gold-tin alloy, because of its excellent resistance to oxidation.

The underlying metallic layers 28, known as ball-limiting metallurgy (BLM), serve as a bonding interface between the solder layer 26 and the surface of the substrate 12. The BLM 28 is comprised of thin layers 30, 32 and 34 of metals which define the base diameter (D) of the hemispherical pad. A number of metals can be used for the composition of the BLM 28. A single layer of nickel comprising layers 30 and 32 will adhere to both a silicon substrate 12 and to the solder layer 26. As an alternative, chromium or titanium, used in layer 30, will adhere to the silicon substrate 12. An additional layer of copper 32, will adhere to the chromium or titanium layer 30 and form an intermetallic bond with the solder layer 26. After the deposition of the nickel or copper layer 32, a thin layer of gold 34 is deposited to provide a passivation layer to prevent oxidation and subsequent poor adhesion between layer 32 and the solder layer 26. After reflowing the circular frustum 24 at an elevated temperature in a hydrogen reflow furnace, a hemispherical solder pad 16 (FIG. 1), is produced, with the gold layer 34 being incorporated into the solder pad 26.

Figure 2A:
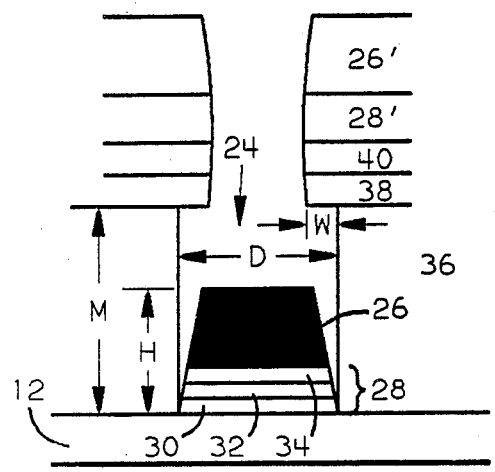
FIGS. 2a–c illustrate three methods of fabricating the universal calibration standard.

Referring to FIG. 2a, a resist lift-off masking technique is illustrated. Before the deposition of the metal layers 26, 30, 32, 34, a lift-off layer of polysulfone 36, a barrier layer 38, and a resist layer 40 are first applied, in succession on substrate 12. Pattern definition is then done using conventional lithographic techniques (optical, electron beam, X-ray, etc.) with the corresponding resist 40. The lift-off structure is formed by reactive ion etching the barrier layer 38 (e.g. methyl siloxane resin or silicon nitride) with a carbon tetrafluoride plasma, followed by an oxygen plasma to etch through the lift-off layer 36. Following the evaporation and deposition of the BLM 28 and solder layer 24, the lift-off of the undesired metal layers 26' and 28' is performed with a solvent (e.g. n-methyl-2-pyrrolidone) that dissolves the lift-off layer 36, leaving the metal frustum 24.

Figure 2B:
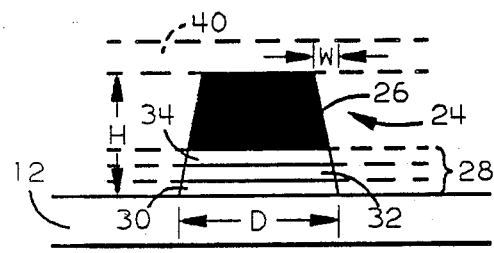

As shown in FIG. 2b, the frustum can also be manufactured using a subtractive etch process. The metal layers 30, 32, 34 and 26 are first evaporated and deposited onto substrate 12. After applying a positive (or negative) photoresist layer 40, conventional lithographic techniques are used to expose the resist areas surrounding each intended metal frustum 24. After the removal of the exposed (or unexposed) resist, the unwanted metal surrounding each intended frustum 24 is removed by either wet or dry etching as known in the art.

Figure 2C:
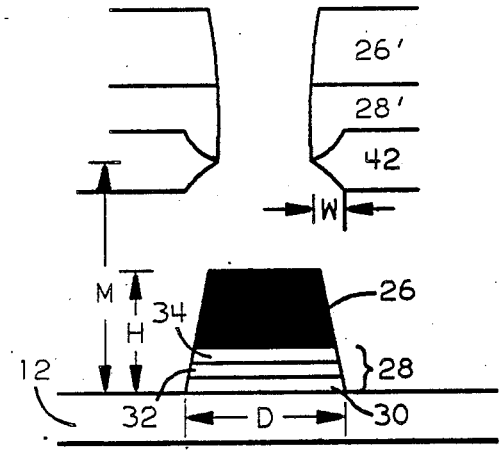

Alternatively, a metal masking technique can be used instead of resist masking techniques. Referring to FIG. 2c, the BLM 28 and solder layer 26 are evaporated and deposited through a metal (e.g. molybdenum) mask 42. This technique is limited to the fabrication of relatively large hemispherical features greater than approximately 50 microns. With the use of a neutral density (ND) filter, the scattering responses produced by these features can be attenuated to a lower level that corresponds to smaller feature sizes (assuming the scattering responses are linear over the entire range). In addition to producing the same net response produced by smaller features, the background surface contamination would also be reduced, possibly to a level below the detection limits of the inspection system.

The critical parameters that must be controlled in the fabrication processes outlined with reference to FIG. 2 are the following:
Base diameter of the BLM—D;
Final metal deposition height—H;
Mask height—M;
Mask overhang—W.

The relationship between these variables is given by the equation:

$$\frac{4W^2H^3}{M^2} - \frac{6DWH^2}{M} + 3D^2H - D^3 = 0.$$

To insure adequate coverage of the entire BLM by the hemispherical solder pad 26, it is suggested that the BLM 28 thickness be no greater than approximately one-sixth of the base diameter D of the BLM 28. This translates to roughly equivalent deposition thicknesses for both the BLM 28 and the solder layer 26.

Figure 3:
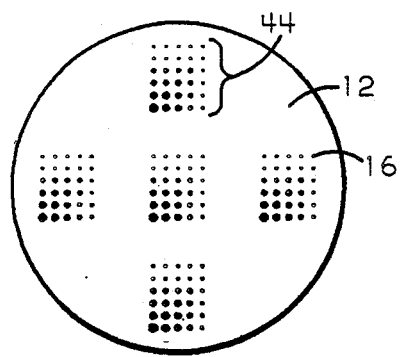
FIG. 3 shows a semiconductor wafer with a plurality of rectilinear arrays of hemispherical pads.

The parameters of major, but less than primary importance, include the size, spacing and arrangement of the features, avoidance of extraneous features, and wafer size. Referring to FIG. 3, there is depicted an arrangement of hemispherical solder pads 16 on the surface of the substrate 12. By using recognizable and patterned (e.g. rectilinear) arrays of features 44, each hemispherical pad 16 can be easily distinguished from low levels of surface contamination. Furthermore, an array has been placed in the center and in each quadrant of the substrate 12 so that the illumination and the detection uniformity of the inspection system can be quickly checked. The spacing between each feature is greater than the resolution capabilities of the detector so that each pad can be resolved from one another.

In the embodiment illustrated in FIG. 3, there are three different feature sizes in each array 44. Feature sizes used range from one to 150 microns in diameter. The advantages of using multiple feature sizes on the same substrate is that multiple sensitivities of the detection system are capable of being established, as well as the linearity of the detection system. While only one feature size can be a perfect hemisphere, unless multiple masking and deposition steps are used, feature sizes up to three times the diameter of this perfect hemisphere can be used. The expected error is less than five percent which is well below the typical size resolution and precision of most inspection systems available.

Because of the permanent nature of the features, the calibration standard can be cleaned repeatedly of any surface contamination by conventional wafer cleaning procedures without harming or altering the size or shape of the features, and without otherwise affecting their ability to scatter or reflect light. In order to minimize accumulated surface contamination on the substrate, it would be advantageous to use a conductive substrate such as metal, heavily doped semiconductor wafer, etc. to minimize electrostatic attraction for particulate contamination.

While the invention has been particularly shown and described with the reference to a preferred embodiment thereof, it will be understood by those skilled in the art that various changes in detail may be made therein without departing from the spirit, scope and teaching of the invention. Accordingly, the invention herein disclosed is to be considered merely as illustrative, and only limited as specified in the claims.

What is claimed is:

1. A test standard for calibrating an optical wafer surface inspection system, said test standard comprising a plurality of pads bonded to a flat, optically reflective substrate, said plurality of pads being hemispherically shaped and comprised of a layer of solder and at least one other metallic layer selected from the group consisting of titanium, copper, gold, chromium, and nickel, whereby the hemispherical pads simulate particulate contamination on the substrate and the wafer surface inspection system can be calibrated independently of the angles of illumination and detection.

2. The test standard as claimed in claim 1 wherein at least one of said pads has a diameter different from the rest of said pads, whereby multiple size sensitivities of said inspection system can be determined.

3. The optical calibration test standard according to claim 1, wherein said hemispherical pads are arranged in at least one patterned array on said test standard.

4. The optical calibration test standard according to claim 1 wherein said flat, optically reflective surface is metallic.

5. The optical calibration test standard according to claim 1 wherein said flat, optically reflective surface is electrically conductive.

6. The optical calibration test standard according to claim 1 wherein said flat, optically reflective surface is a semiconductor wafer.

7. The optical calibration test standard according to claim 1 wherein said solder is selected from the group consisting of gold, tin, lead, indium and bismuth.

8. The calibration test standard as recited in claim 1 wherein said hemispherical pads have diameters in the range oe to 150 microns.

* * * * *

UNITED STATES PATENT AND TRADEMARK OFFICE
CERTIFICATE OF CORRECTION

PATENT NO. : 4,636,073
DATED : Jan. 13, 1987
INVENTOR(S) : Randall R. Williams

It is certified that error appears in the above-identified patent and that said Letters Patent are hereby corrected as shown below:

In the Abstract:

Column 2, line 3 - Change "liquid" to --light--.

In the Claims:

Column 2, Claim 8, line 18 - Change "oe" to --one--.

Signed and Sealed this

Thirty-first Day of March, 1987

Attest:

DONALD J. QUIGG

Attesting Officer

Commissioner of Patents and Trademarks